US009162983B2

(12) United States Patent
Bauta et al.

(10) Patent No.: US 9,162,983 B2
(45) Date of Patent: Oct. 20, 2015

(54) REACTIVATORS OF ORGANOPHOSPHOROUS INHIBITED ACETYLCHOLINESTERASE

(71) Applicant: Southwest Research Institute, San Antonio, TX (US)

(72) Inventors: William E. Bauta, San Antonio, TX (US); William R. Cantrell, Jr., San Antonio, TX (US); Michael W. Tidwell, Lakehills, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/284,890

(22) Filed: May 22, 2014

(65) Prior Publication Data

US 2014/0350262 A1    Nov. 27, 2014

Related U.S. Application Data

(60) Provisional application No. 61/826,161, filed on May 22, 2013.

(51) Int. Cl.
    *C07D 215/38* (2006.01)
(52) U.S. Cl.
    CPC ................................ *C07D 215/38* (2013.01)
(58) Field of Classification Search
    CPC ......................... C07D 215/38; A01B 12/006
    See application file for complete search history.

(56) References Cited

U.S. PATENT DOCUMENTS

| | | | |
|---|---|---|---|
| 3,045,025 | A | 7/1962 | Hackley et al. |
| 5,929,093 | A | 7/1999 | Pang et al. |
| 5,998,460 | A | 12/1999 | Brossi et al. |
| 8,653,108 | B1 | 2/2014 | McHardy et al. |
| 8,772,345 | B2 | 7/2014 | McHardy et al. |
| 8,871,789 | B2 * | 10/2014 | Kristie et al. ............... 514/311 |
| 2008/0262227 | A1 | 10/2008 | Slanina et al. |
| 2013/0035351 | A1 | 2/2013 | McHardy et al. |
| 2014/0066421 | A1 | 3/2014 | McHardy et al. |
| 2015/0005328 | A1 | 1/2015 | McHardy et al. |

FOREIGN PATENT DOCUMENTS

WO       2006032851 A1    3/2006

OTHER PUBLICATIONS

H.P. Benschop et al, Med.Prot. Chem.-Warf. Agents, [Pap Symp] 1976. Meeting date 1974, 120-33. Almqvist & Wiksell, Stockholm, Sweden.
Botta, et al., "Oxime Amides as a Novel Zinc Binding Group in Histone Deacetylase Inhibitors: Synthesis, Biological Activity, and Computational Evaluation," Journal of Medical Chemistry 2011, 54, 2165-2182.
B.A.Chabner, et al "Antineoplastic Agents", Goodman & Gilman's The Pharmacological Basis of Therapeutics, 11 Edition 2006, Section IX, Chemotherapy of Neoplastic Disease; downloaded Oct. 25, 2011 from http://lib.myilibrary.com.
A.F. Childs, et al, "The Reactivation by Oximer and Hydroxamic Acids of Cholinesterase Inhibited by Organo-Phosphorus Compounds", 10 British Journal of Pharmacology, 462-465 (1955).
K. Chow, et al "Engineering of Pharmaceutical Materials: An Industrial Perspective", Journal of Pharmaceutical Sciences, vol. 97, No. 9, Aug. 2008, pp. 2855-2877.
F. Degorre, et al, "Sulfur Derivatives of 2-Oxopropanal Oxime as Reactivators of Organophosphate-Inhibited Acetylcholinesterase In Vitro: Synthesis and Structure-Reactivity Relationships"; 31 Journal of Medicinal Chemistry, 757-763 (1988).
Ellman, et al; "A New and Rapid Colorimetric Determination of Acetylcholinesterase Activity"; Biochemical Pharmacology, 1961, vol. 7, pp. 88-95, Pergamon Press Ltd., printed in Great Britain.
P.L. Gould, "Salt Selection for Basic Drugs", International Journal of Pharmaceutics, 33 (1986) 201-217, pp. 201-217.
Greene, "Protective Groups in Organic Chemistry," A Wiley-Interscience Publication, John Wiley & Sons, Inc. 1981 (cover page and table of contents provided).
Greene, et al., "Protective Groups in Organic Chemistry," Second Edition, A Wiley-Interscience Publication, John Wiley & Sons, Inc. 1991 (cover page and table of contents provided).
J. Kassa, et al "A Complex Process of the Development of New Acetylcholines Reactivators—From Prediction to In Vivo Evaluation", Journal of Medical Chemical,Biological and Radiological Defense, vol. 3, 2005, pp. 1-9.
Z. Kovarik, et al "Oximes: Reactivators of Phosphorylated Acetylcholinesterase and Antidotes in Therapy Against Tabun Poisoning", 175 Chemico-Biological Interactions 173-179 (2008).
S.L. Morissette, et al, "High-throughput Crystallization: Polymorphs, Salts, Co-Crystals and Solvates of Pharmaceutical Solids", Advanced Drug Delivery Reviews, 56, 275-300 (2004).
K.R. Morris, et al, "An integrated Approach to the Selection of Optimal Salt Form for a New Drug Candidate", International Journal of Pharmaceutics 105 (1994) pp. 209-217.
R. Odzak et al, "Evaluation of Monoquaternary Pyridinium Oximes Potency to Reactivate Tabun-Inhibited Human Acetylcholinesterase" 233 Toxicology, 85-96 (2007).
J.H. Poupaert, "Drug Design: Basic Principles and Applications", Encyclopedia of Pharmaceutical Technology, 2007,pp. 1362-1369.
I. Somin et al., 2 Khimilo-Farmatsevticheskii Zhurnal 39-44 (1968); CAS Abstract Accession No. 1969:19526 (1969); US Office Action, mail date Dec. 19, 2012, in related U.S. Appl. No. 13/197,550.
I. Somin, et al, 13 Zhurnal Organicheskoi Khimi 910-918 (1977); US Office Action, mail date Dec. 19, 2012, in related U.S. Appl. No. 13/197,550.
I. Somin et al, 43 Zhurnal Obshchei Khimii 331-335 (1973); US Office Action, mail date Dec. 19, 2012, in related U.S. Appl. No. 13/197,550.
O. Soukup, et al, "Novel Acetylcholinesterase Reactivator K112 and its Cholinergic Properties", Biomedicine & Pharmacotherapy 64 (2010), pp. 541-545.
S.Takada, et al, "Synthesis and Structure-Activity Relationships of Fused Imidazopyridines: A New Series of Benzodiazepine Receptor Ligands", Journal of Medicinal Chemistry Chem. 1996, 39, 2844-2851, Abstract only downloaded from web Jul. 22, 2014. http://pubs.acs.org/doi/as/10.1021.

(Continued)

*Primary Examiner* — D M Seaman
(74) *Attorney, Agent, or Firm* — Grossman, Tucker et al.

(57) ABSTRACT

The present invention relates to organophosphate-inhibited acetylcholinesterase (AChE) reactivators with central nervous system (CNS) bioavailability and their associated methods of preparation including their use for treatment of exposure to AChE inhibitors such as an organophosphate (OP) insecticides and nerve agents.

12 Claims, 13 Drawing Sheets

(56) References Cited

OTHER PUBLICATIONS

Wang, et al., "Evaluation of the MDR-MDCK cell line as a permeability screen for the blood-brain barrier," International Journal of Pharmaceutics 288 (2005) 349-359.

US Office Action, mail dated Dec. 19, 2012, issued in related U.S. Appl. No. 13/197,550.

US Office Action, mail dated Jul. 31, 2013, issued in related U.S. Appl. No. 13/197,550.

US Notice of Allowance, mail date Mar. 28, 2014 issued in related U.S. Appl. No. 13/197,550.

US Office Action, mail dated Jul. 31, 2013, issued in related U.S. Appl. No. 13/474,399.

US Notice of Allowance, mail date Nov. 5, 2013 issued in related U.S. Appl. No. 13/474,399.

* cited by examiner

Structure Type 1a

Structure Type 1b

*FIG. 5*

Structure Type 1c

Structure Type 1d

FIG. 6

Structure Type 2a

Structure Type 2b

*FIG. 7*

Structure Type 2c

Structure Type 2d

*FIG. 8*

Structure Type 3a

Structure Type 3b

*FIG. 9*

Structure Type 3c

Structure Type 3d

*FIG. 10*

Structure Type 4a

Structure Type 4b

*FIG. 11*

Structure Type 4c

Structure Type 4d

*FIG. 12*

Structure Type 4e

Structure Type 4f

*FIG. 13*

REACTIVATORS OF ORGANOPHOSPHOROUS INHIBITED ACETYLCHOLINESTERASE

CROSS REFERENCE TO RELATED APPLICATIONS

The present application claims the benefit of the filing date of U.S. Provisional Application Ser. No. 61/826,161, filed May 22, 2013, the teachings of which are incorporated herein by reference.

GOVERNMENT RIGHTS CLAUSE

This invention was made with United States Government support under Contract No. HDTRA1-10-00041 awarded by the Defense Threat Reduction Agency. The Government has certain rights in this invention.

FIELD OF THE INVENTION

The present invention relates to organophosphate-inhibited acetylcholinesterase (AChE) reactivators with central nervous system (CNS) bioavailability and their associated methods of preparation including their use for treatment of exposure to AChE inhibitors such as an organophosphate (OP) insecticides and nerve agents.

BACKGROUND

Signal transmission at synapses is mediated by the neurotransmitter acetylcholine. Such signaling may be discontinued by AChE, which catalyzes the hydrolysis of acetylcholine. AChE-inhibiting chemicals may prevent the breakdown of acetylcholine, thereby disrupting normal nervous system activity through an excess of acetylcholine at synapses. For example, certain classes of pesticides, such as organophosphates and carbamates, may result in toxicity through AChE inhibition. Organophosphate chemical warfare agents such as sarin and tabun also function through AChE inhibition. Accordingly, if an individual may be exposed to such inhibitors, there remains a need to prophylactically or therapeutically mitigate or reverse such cholinergic toxicity. Individuals or animals who have been exposed to a cholinesterase inhibitor may currently be treated with an AChE reactivator (antidote) such as pralidoxime in combination with atropine, a competitive agonist for acetylcholine at muscarinic receptors, and an anti-seizure medication such as benzodiazepine. In addition, AChE reactivators may be employed medicinally to treat various ailments such as Alzheimer's disease.

DETAILED DESCRIPTION

As alluded to above, the present disclosure is directed at the formation of certain AChE reactivators. Such reactivators may be used to prophylactically and/or therapeutically treat intoxication in a person or animal due to the presence of a cholinesterase inhibitor, such as a phosphorous containing cholinesterase inhibitor. The reactivators may also be used for medicinal purposes.

It is therefore worth pointing out that OPs may act as hemi-substrates of cholinesterase by specifically phosphorylating the active site serine. As the rate of hydrolysis of the phosphoryl or phosphonyl enzyme is relatively slower than deacylation of acytylcholine, OPs are effectively irreversible cholinesterase inhibitors. OPs have also been developed as chemical weapon systems, and relatively potent insecticides, due to their inhibition of the insects' flight muscle cholinesterase, with resulting paralysis and death. It may therefore be appreciated that intoxication by anti-cholinesterase compounds may develop following accidental exposure to organophosphorus insecticides and/or other associated chemical agents. Furthermore, the overall pharmacologic effect of AChE inhibitors is due to the inhibition of cholinesterase enzymes throughout the body.

Figure 1:
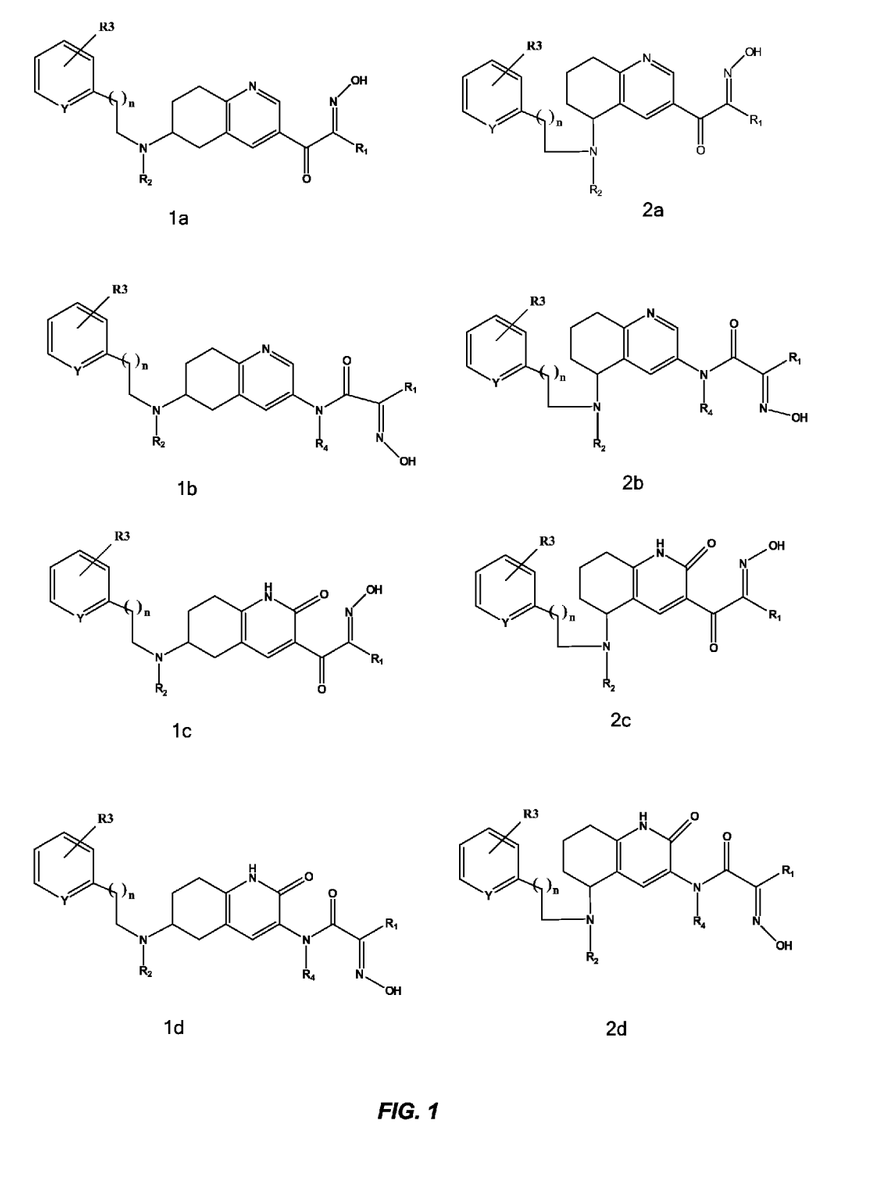
FIG. 1 illustrates the general structures of reactivator compounds 1a, 2a, 1b, 2b, 1c, 2c, 1d and 2d.
Figure 2:
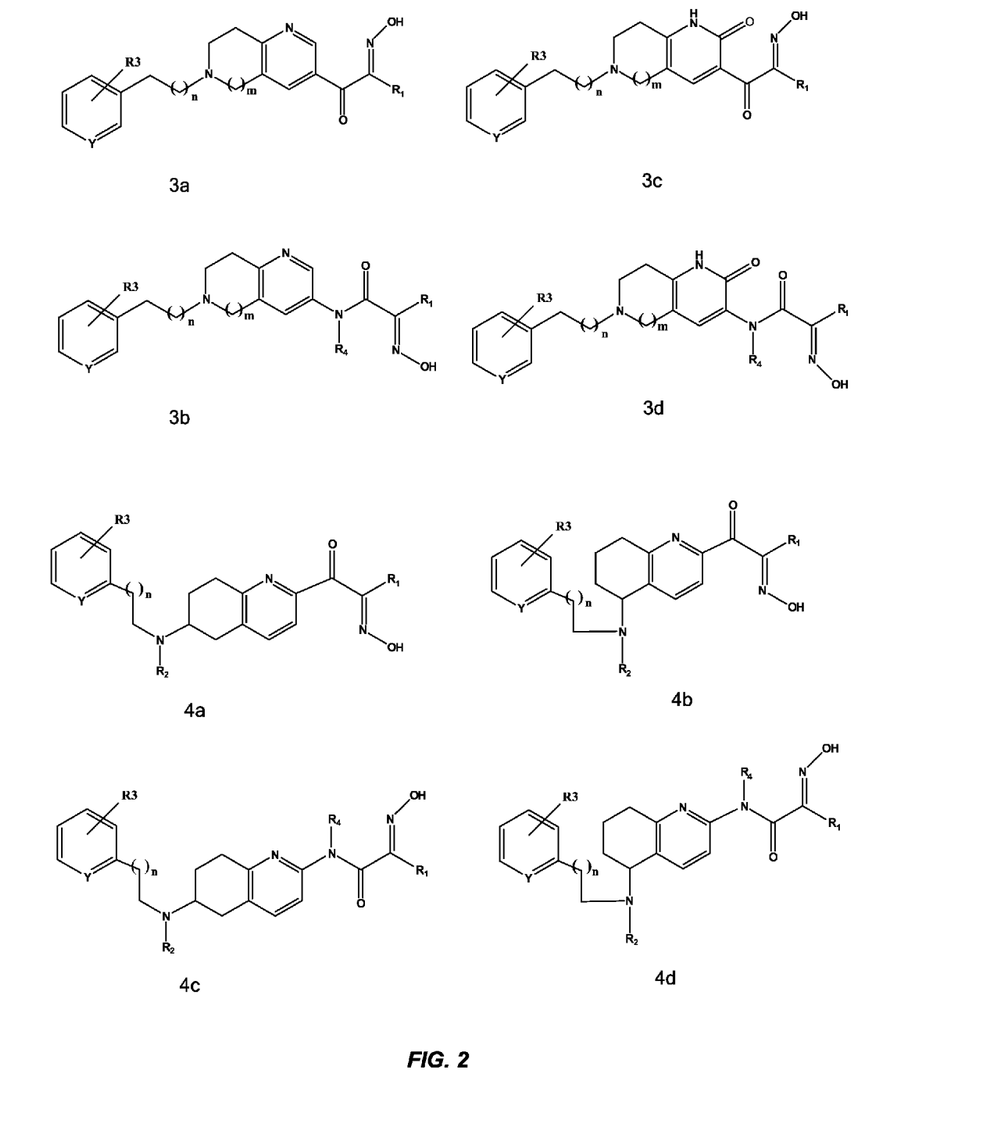
FIG. 2 illustrates the general structures of reactivator compounds 3a, 3b, 3c, 3d 4a, 4b, 4c and 4d.
Figure 3:
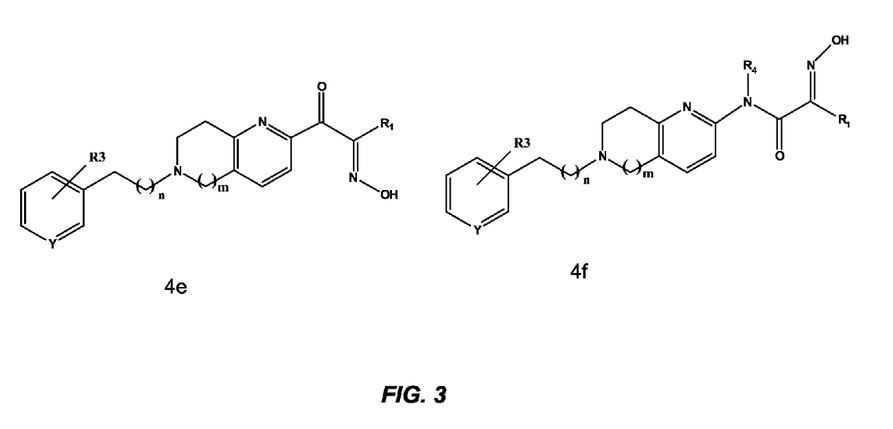
FIG. 3 illustrated the general structure of reactivator compounds 4e and 4f.

The reactivator structures developed herein, identified as structures 1a, 2a, 1b, 2b, 1c, 2c, 1d, 2d, 3a, 3c, 3b, 3d, 4a, 4b, 4c, 4d, 4e and 4f are illustrated in FIGS. 1-3. It should be noted that enantiomers of the indicated structures are contemplated for use herein as reactivators as well as salt forms, which will include mono or di-salts in view of the presence of two basic nitrogens.

In the indicated formulae in FIGS. 1-3 the following applies: $R_1$ is a ketone functionality (C(O)R) or hydrogen, where R may be a H or an alkyl group. The alkyl group may be linear or branched and contain up to five carbon atoms. For example, the alkyl group may be defined as $C_xH_{2x+1}$ and where x has a value of up to 5. The alkyl groups may therefore include the following groups: methyl (—$CH_3$), ethyl (—$CH_2$—$CH_3$), propyl (—$CH_2$—$CH_2$—$CH_3$), isopropyl (—$CHC(CH_3)_2$), butyl (—$CH_2$—$CH_2$—$CH_2$—$CH_3$), sec-butyl (—$CH(CH_3)$—$CH_2CH_3$), and isobutyl (—$CH_2$—$CH(CH_3)_2R_2$ and $R_4$ are H or an alkyl group which again may be linear or branched and contain up to five carbon atoms. $R_3$, which is attached to the aromatic ring may be H, an electron withdrawing group (e.g., halogen, trifluromethyl) or an electron donating group (e.g., alkyl, amino, substituted amino and aryl amido). The aromatic ring to which $R_3$ is attached may also amount to a heterocyclic six-membered ring containing carbon and nitrogen (Y is carbon or nitrogen). The value of n may be 0-4 which therefore may define the number of carbon atoms (e.g. methylene groups). The value of m may be 0-1 and also defines the number of carbon atoms (e.g. methylene groups).

One preferred route for reactivator synthesis herein is set out below:

3'-Nitro-7',8'-dihydro-5'H-spiro[1,3-dioxolane-2,6'-quinoline]

The title compound was prepared according to the procedure of Takada (*J. Med. Chem.* 1996, 39, 2844-2851). A 350 mL pressure vessel, equipped with a magnetic stir bar, was charged with 1-methyl-3,5-dinitropyridin-2(1H)-one (5.0 g, 25.1 mmol) and 1,4-dioxaspiro[4.5]decan-8-one (4.7 g, 30.1 mmol). Ammonia in MeOH (1M, 200 mL) was added, the vessel was sealed with a screw cap, and the mixture was heated to 60° C. and stirred for 17 hours. The reaction mixture was concentrated and the residue was partitioned with ethyl acetate (200 mL) and water (200 mL). The layers were separated and the aqueous portion was extracted with ethyl acetate (2×100 mL). The organic portions were combined, dried (Na$_2$SO$_4$), filtered, and concentrated. The residue was purified by silica gel chromatography (7/3, hexanes/ethyl acetate) to afford the title compound (4.85 g, 82%).

3-Nitro-7,8-dihydroquinolin-6(5H)-one

The title compound was prepared according to the procedure of Pelcman (WO2006032851, 1996). A 250 mL flask, equipped with a magnetic stirbar and reflux condenser, was charged with 3'-nitro-7',8'-dihydro-5'H-spiro[1,3-dioxolane-2,6'-quinoline] (4.75 g, 20.1 mmol), acetone (65 mL), hydrochloric acid (2N (aq), 42 mL), and water (21 mL). The mixture was heated to 65° C. for 1 h, then to 80° C. for 30 minutes. The mixture was cooled to ambient temperature and neutralized with saturated NaHCO$_3$ (aq) until pH=8. The mixture was extracted with EtOAc (3×) and the combined organic portions were dried (Na$_2$SO$_4$) and concentrated. The residue was purified by silica gel chromatography (30 to 60% EtOAc in hexanes) to afford the title compound (2.5 g, 65%).

N-Methyl-3-nitro-N-(2-phenylethyl)-5,6,7,8-tetrahydroquinolin-6-amine

A 100 mL flask, equipped with a magnetic stirbar, was charged with 3-nitro-7,8-dihydroquinolin-6(5H)-one (2.5 g, 13.0 mmol), N-methyl-2-phenylethanamine (1.76 g, 13.0 mmol), and 1,2-dichloroethane (73 mL). Sodium triacetoxyborohydride (4.13 g, 19.5 mmol) was added as a solid. The mixture was stirred at ambient temperature for 40 hours. Saturated NaHCO$_3$ (aq) was added until the pH=8. The mixture was extracted with dichloromethane (3×50 mL). The combined organic portions were dried (Na$_2$SO$_4$) and concentrated. The residue was purified by silica gel chromatography (0 to 10% MeOH in dichloromethane) to provide the title compound (0.73 g, 18%). $^1$H NMR (400 MHz, CD$_3$OD), δ9.16 (d, 1H, J=2.6), 8.13 (d, 1H, J=2.6), 7.30-7.17 (m, 5H), 3.19 (ddd, 2H, J=19, 6, 4), 2.96-2.89 (m, 6H), 2.45 (s, 3H), 2.21-2.12 (m, 2H), 1.89-1.84 (m, 1H). MS [M+H]$^+$=312.2 m/z.

N$^6$-methyl-N$^6$-(2-phenylethyl)-5,6,7,8-tetrahydroquinoline-3,6-diamine A 100 mL flask, equipped with a magnetic stirbar, was charged with methyl-3-nitro-N-(2-phenylethyl)-5,6,7,8-tetrahydroquinolin-6-amine (0.71 g, 2.28 mmol), Pd/C (10% w/w, 0.15 g, 0.14 mmol), and EtOH (10 mL). The flask was capped with a balloon filled with hydrogen and the mixture was stirred at ambient temperature for 2 hours. The mixture was filtered over Celite (5 g) to remove the catalyst. The filtrate was concentrated to afford the title compound. The material was used in the next step without further purification.

N-{6-[Methyl(phenethyl)amino]-5,6,7,8-tetrahydroquinolin-3-yl}-3-oxobutanamide

A 10 mL vial, equipped with a magnetic stirrer, was charged with N⁶-methyl-N⁶-(2-phenylethyl)-5,6,7,8-tetrahydroquinoline-3,6-diamine (79 mg, 0.281 mmol), 2,2,6-trimethyl-4H-1,3-dioxin-4-one (48 mg, 0.337 mmol), and toluene (3 mL). The vial was sealed and heated in a microwave reactor at 120° C. for 30 min. The reaction mixture was concentrated and the residue was purified by silica gel chromatography (0 to 100% acetone in hexanes) to give the title compound (73 mg, 71%). MS [M+H]⁺=366.2 m/z.

(E)-2-(Hydroxyimino)-N-{6-[methyl(phenethyl) amino]-5,6,7,8-tetrahydroquinolin-3-yl}-3-oxobutanamide hydrochloride A 20 mL vial was charged with N-{6-[methyl(phenethyl)-amino]-5,6,7,8-tetrahydroquinolin-3-yl}-3-oxobutanamide (73 mg, 0.200 mmol) and glacial acetic acid (1 mL). A solution of sodium nitrite (19 mg, 0.269 mmol) in water (0.3 mL) was added and the mixture was stirred at ambient temperature for 19 hours. The reaction mixture was concentrated and the residue was purified by silica gel chromatography (0 to 30% MeOH in dichloromethane). The purified free base was dissolved in dichloromethane (6 mL) and HCl (1N (aq) in Et₂O, 0.15 mL) was added. The reaction mixture was concentrated to give the title compound (53 mg, 61%). ¹H NMR (400 MHz, CD₃OD), δ8.95 (s, 1H), 8.28 (s, 1H), 7.39-7.25 (m, 5H), 3.95 (br s, 1H), 3.65-3.05 (m, 10H), 3.05 (s, 3H), 2.50-2.45 (m, 1H), 2.25-2.05 (m, 1H), 1.95 (s, 3H). MS [M+H]⁺=395.2 m/z.

Figure 4:
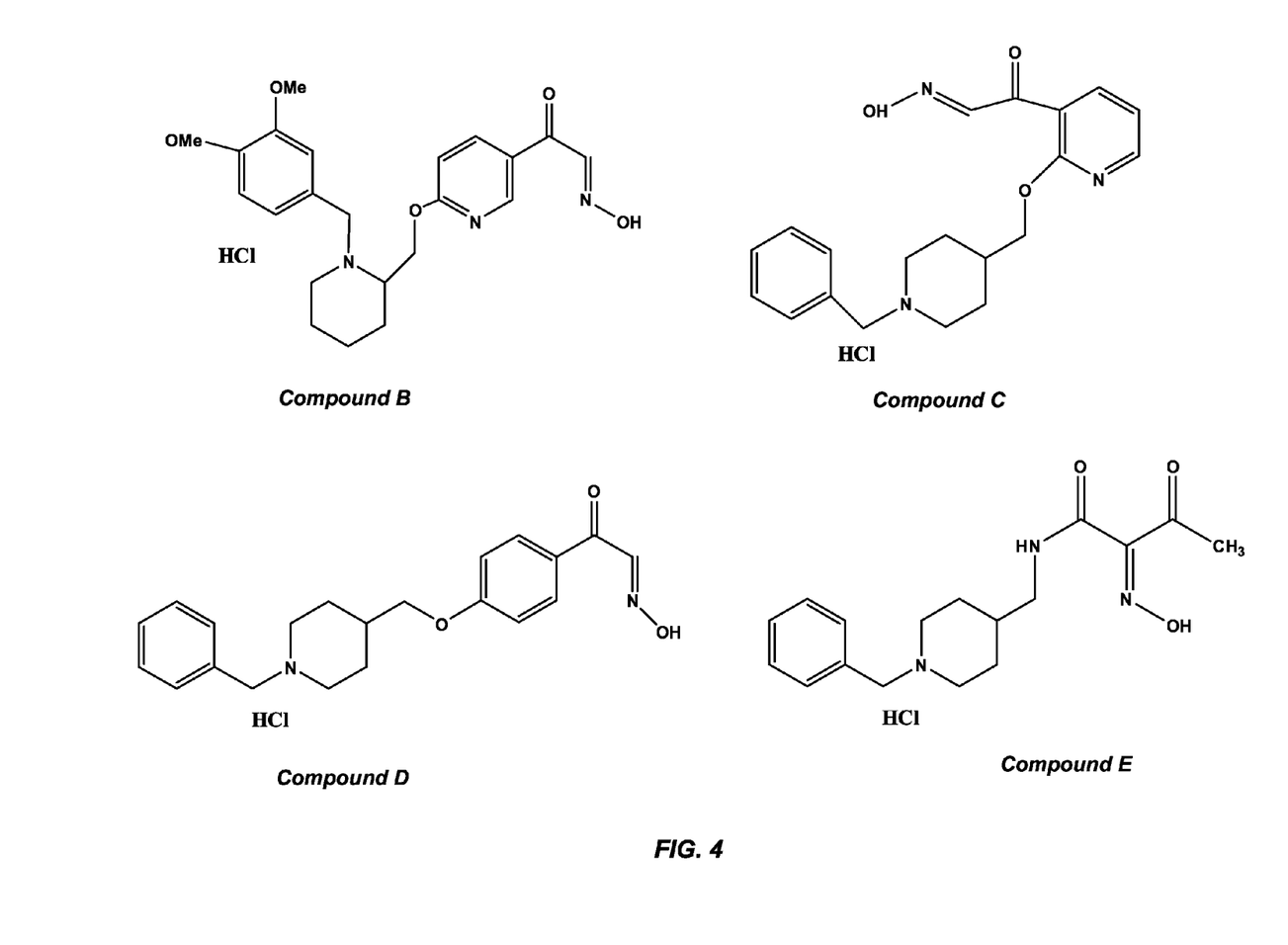
FIG. 4 illustrates reactivator compounds employed for comparative studies reported in Table 1.

The above referenced (E)-2-(Hydroxyimino)-N-{6-[methyl(phenethyl)amino]-5,6,7,8-tetrahydroquinolin-3-yl}-3-oxobutanamide hydrochloride (Compound A) was then evaluated for in vitro reactivator activity and selectivity for the OP-inhibited enzyme. Specifically, the ability of (E)-2-(Hydroxyimino)-N-{6-[methyl(phenethyl)amino]-5,6,7,8-tetrahydroquinolin-3-yl}-3-oxobutanamide hydrochloride to reactivate AChE inhibited by a nerve agent at a 20 mM concentration after about 4.0 hours was evaluated versus known reactivators. The results are listed below in Table 1 in comparison to Compounds B, C, D and E, whose structures are illustrated in FIG. 4.

TABLE 1

| | In Vitro Reactivator Comparisons | |
|---|---|---|
| Compound | AChE (%) Reactivated After Four Hours | Equilibrium Constant ($K_i$) For Native AChE Inhibition |
| A | 96.34 | 1108 |
| B | 71.26 | 233 |
| C | 50.13 | 180 |
| D | 37.80 | 31 |
| E | 23.90 | 2300 |

It should be noted that the equilibrium constant for AChE inhibition in Table 1 is reference to the equilibrium constant $K_i$=[AChE][Oxime]/[AChE-oxime complex]. Accordingly $K_i$ is for uninhibited AChE. The higher the number, the less the native enzyme is inhibited by the reactivator compound, which is what one desires to achieve: reactivation of the inhibited AChE but little inhibition of native enzyme activity.

Figure 5:
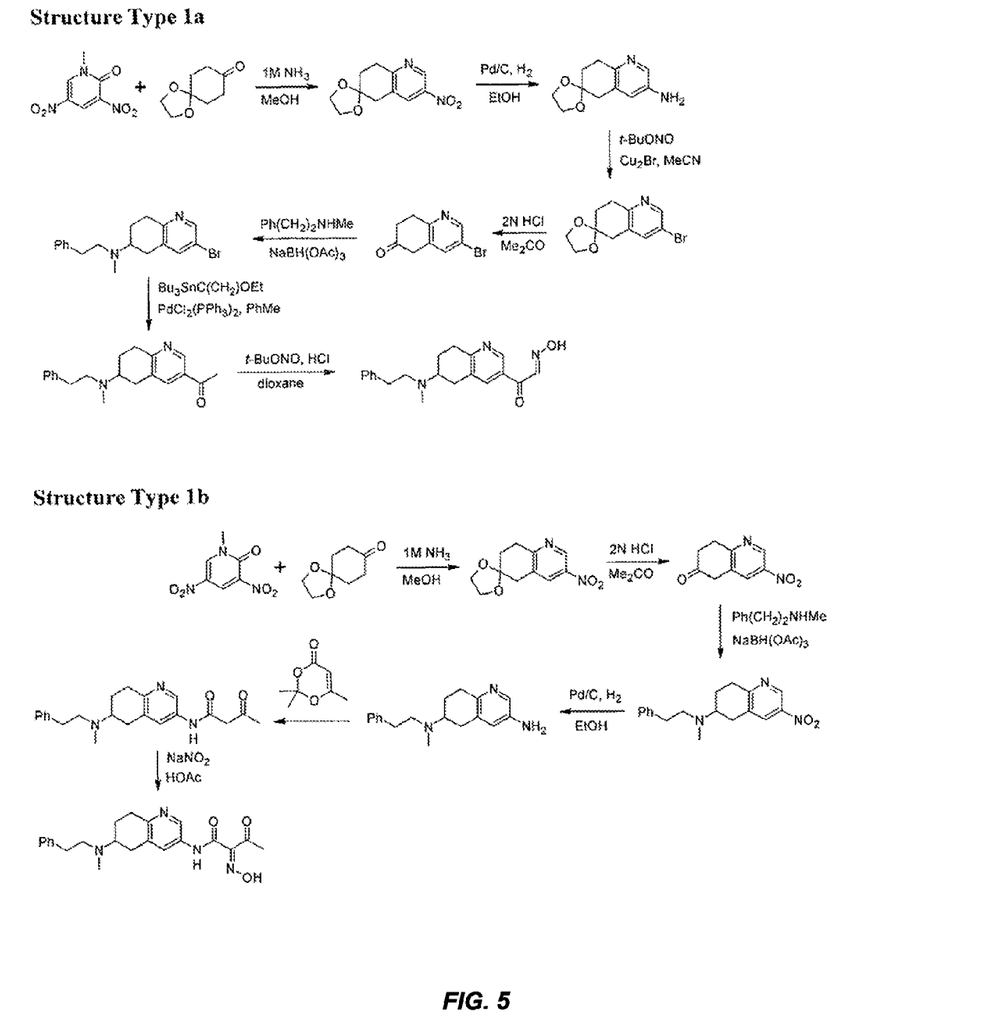
FIG. 5 illustrates the contemplated synthetic routes for Structure Type 1a and Structure Type 1b.
Figure 6:
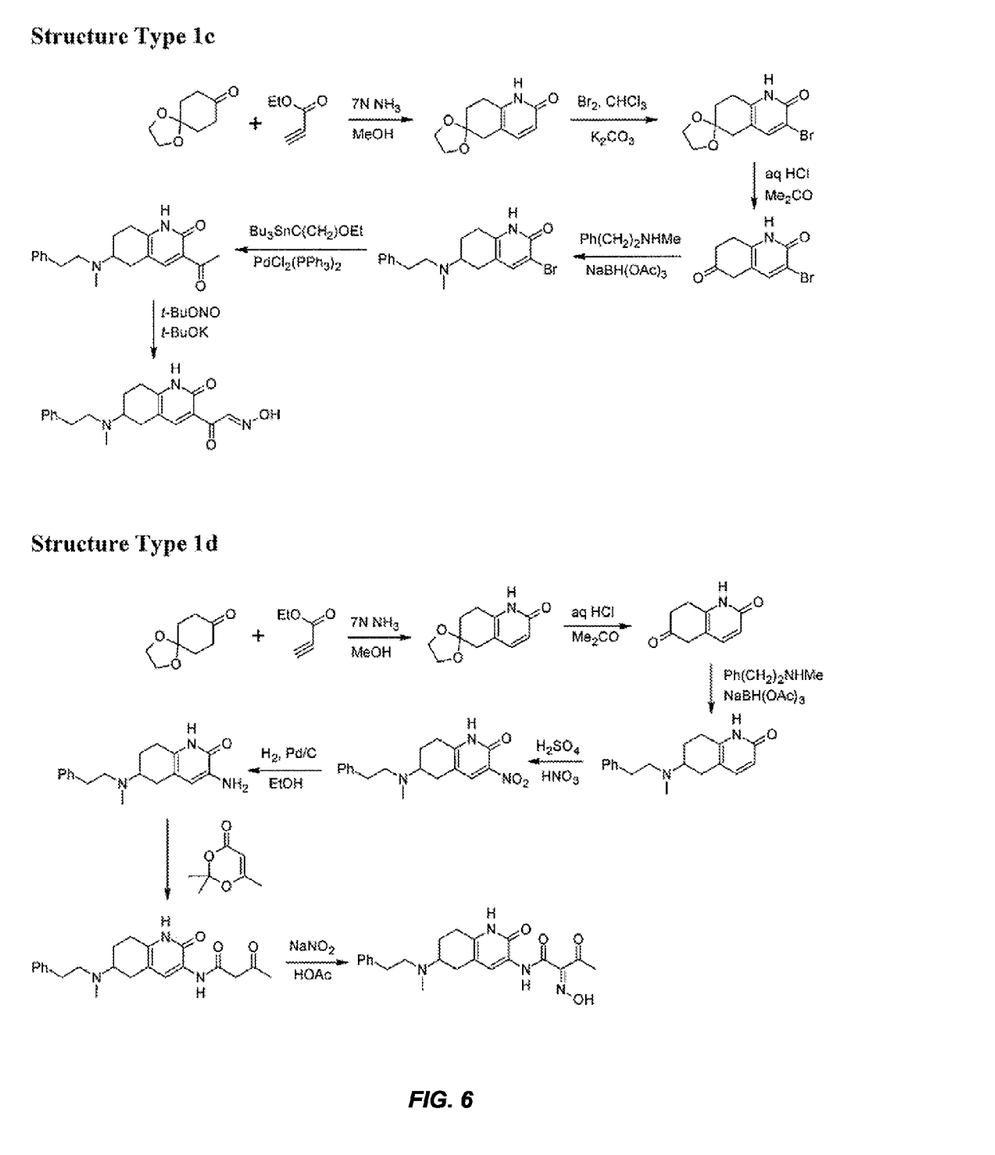
FIG. 6 illustrates the contemplated synthetic routes for Structure Type 1c and Structure Type 1d.
Figure 7:
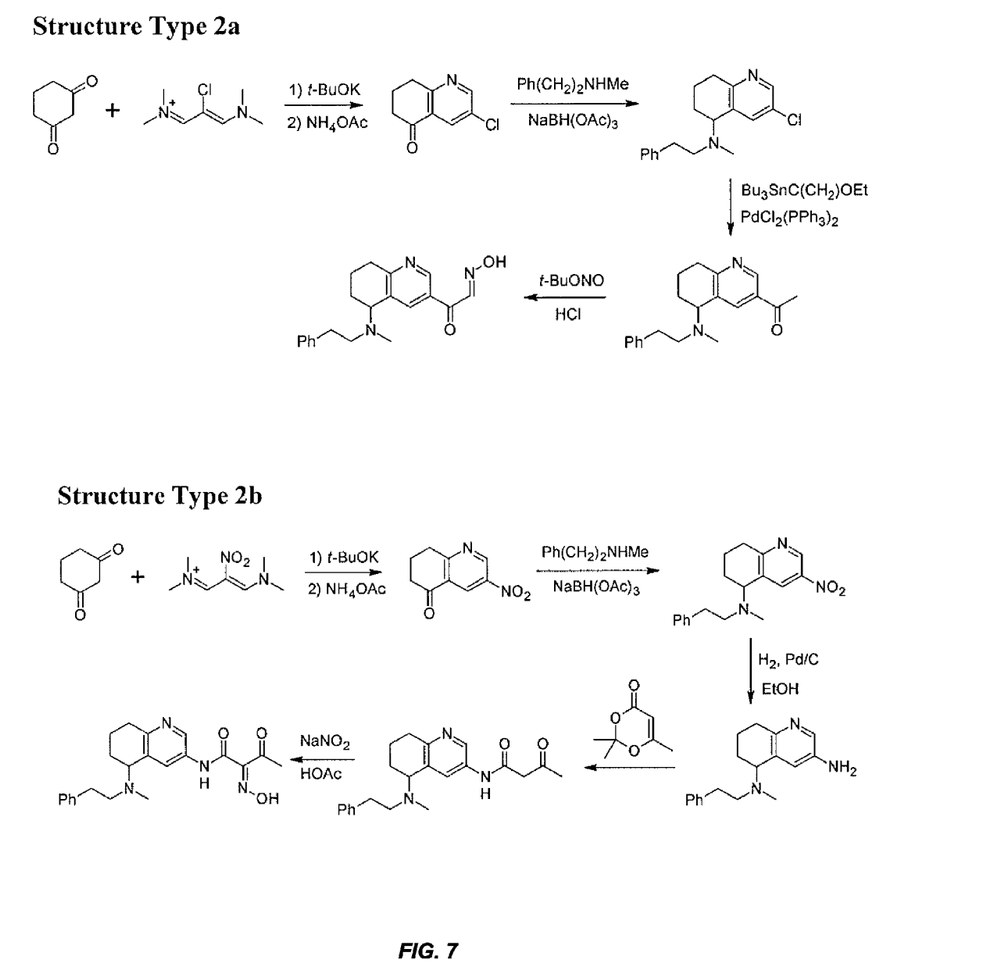
FIG. 7 illustrates the contemplated synthetic routes for Structure Type 2a and Structure Type 2b.
Figure 8:
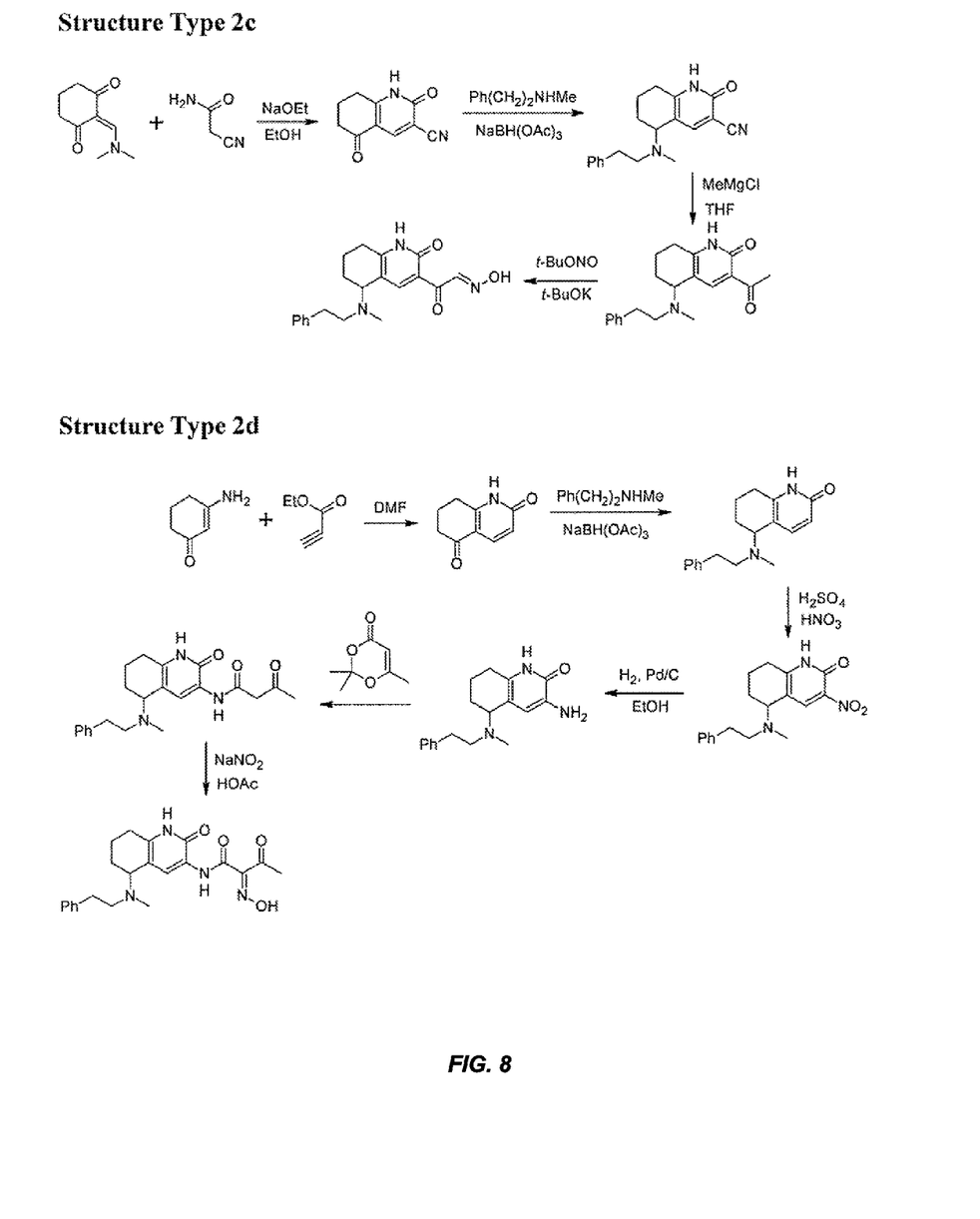
FIG. 8 illustrates the contemplated synthetic routes for Structure Type 2c and Structure Type 2d.
Figure 9:
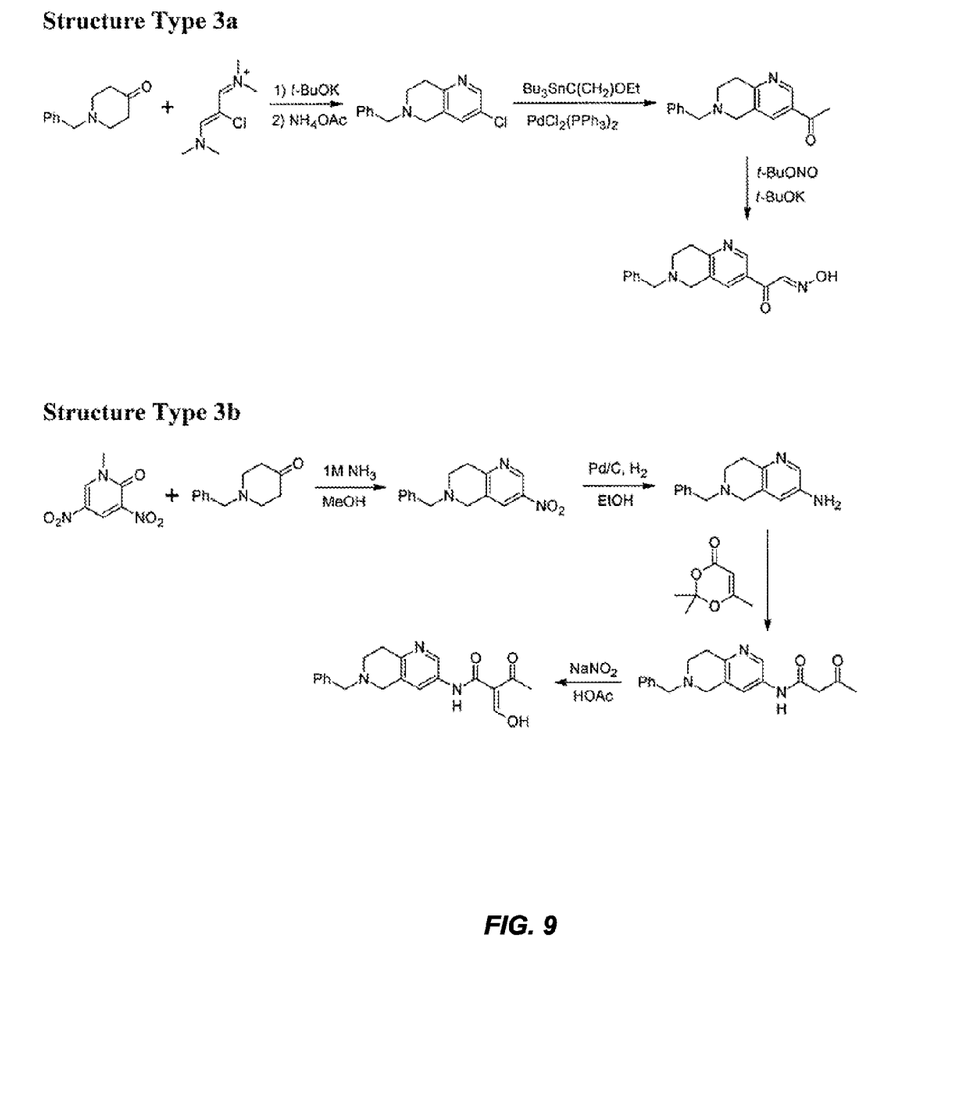
FIG. 9 illustrates the contemplated synthetic routes for Structure Type 3a and Structure Type 3b.
Figure 10:
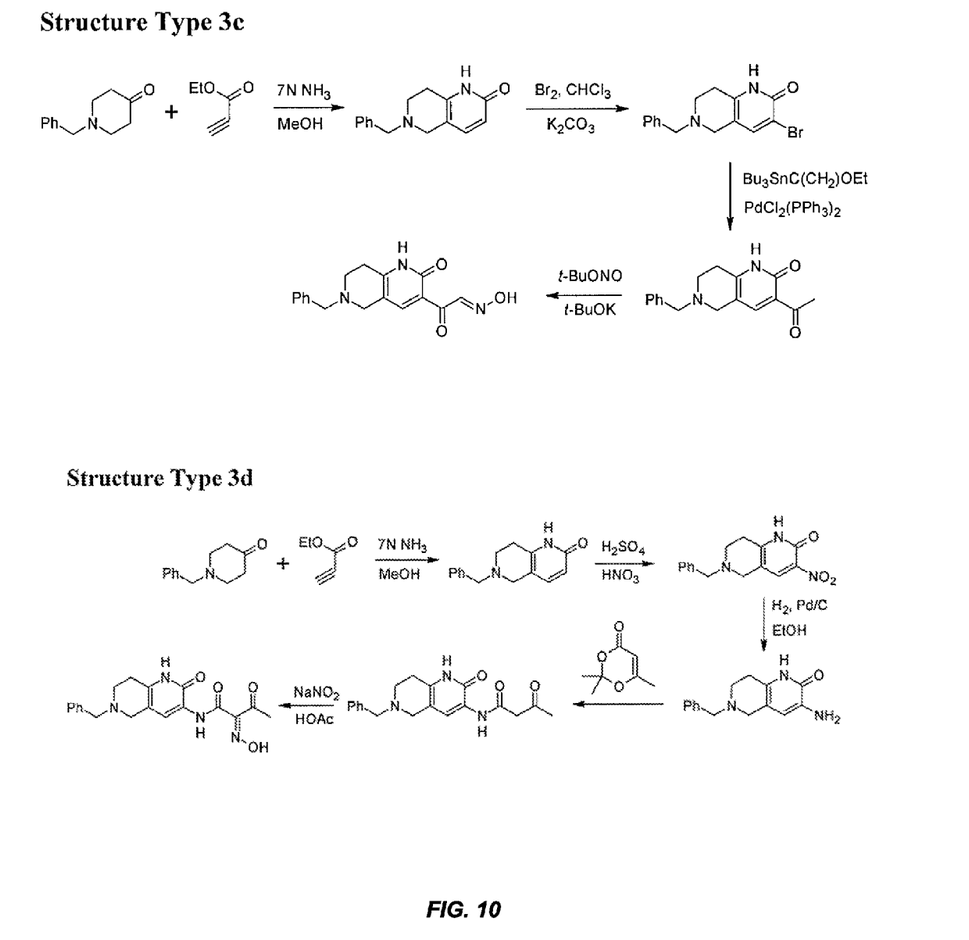
FIG. 10 illustrates the contemplated synthetic routes for Structure Type 3c and Structure Type 3d.
Figure 11:
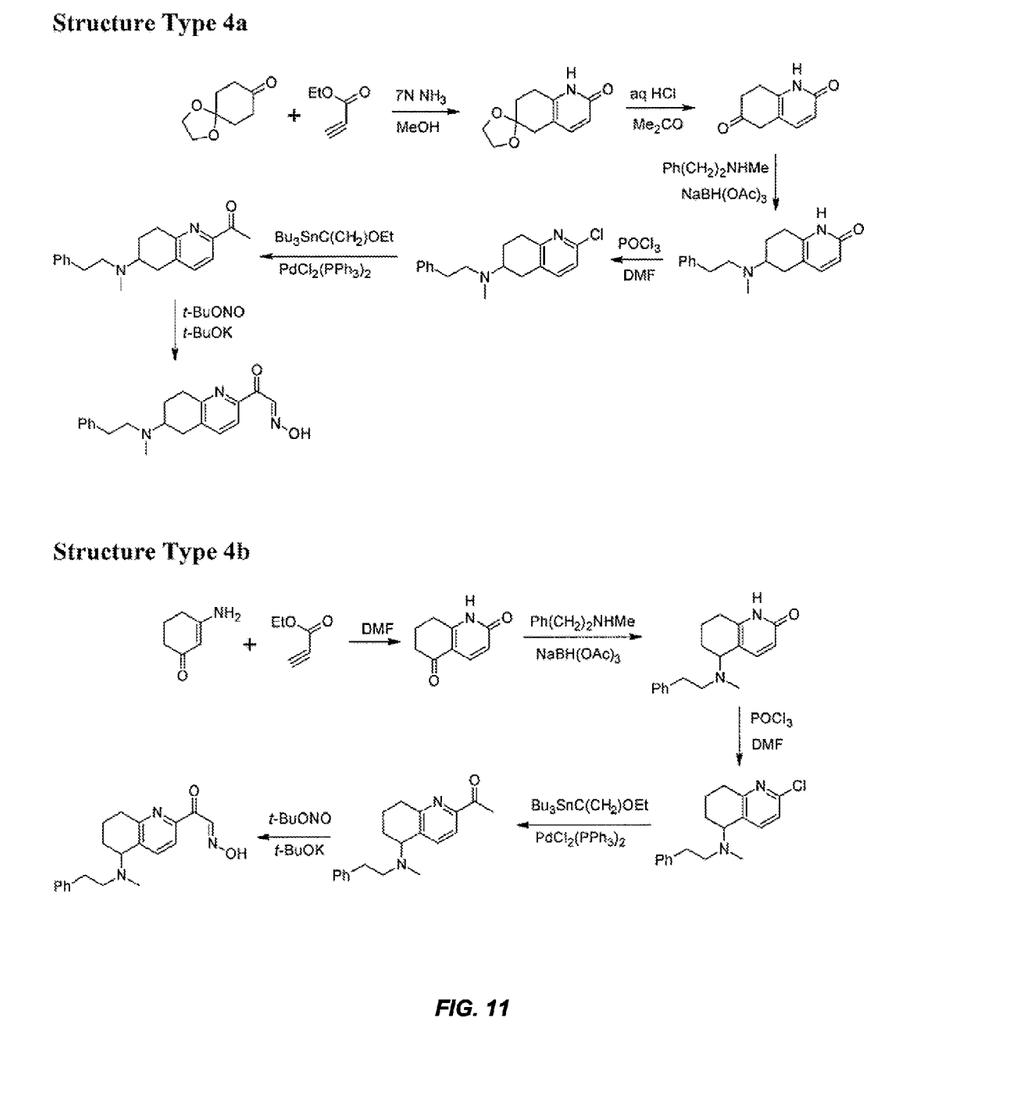
FIG. 11 illustrates the contemplated synthetic routes for Structure Type 4a and Structure Type 4b.
Figure 12:
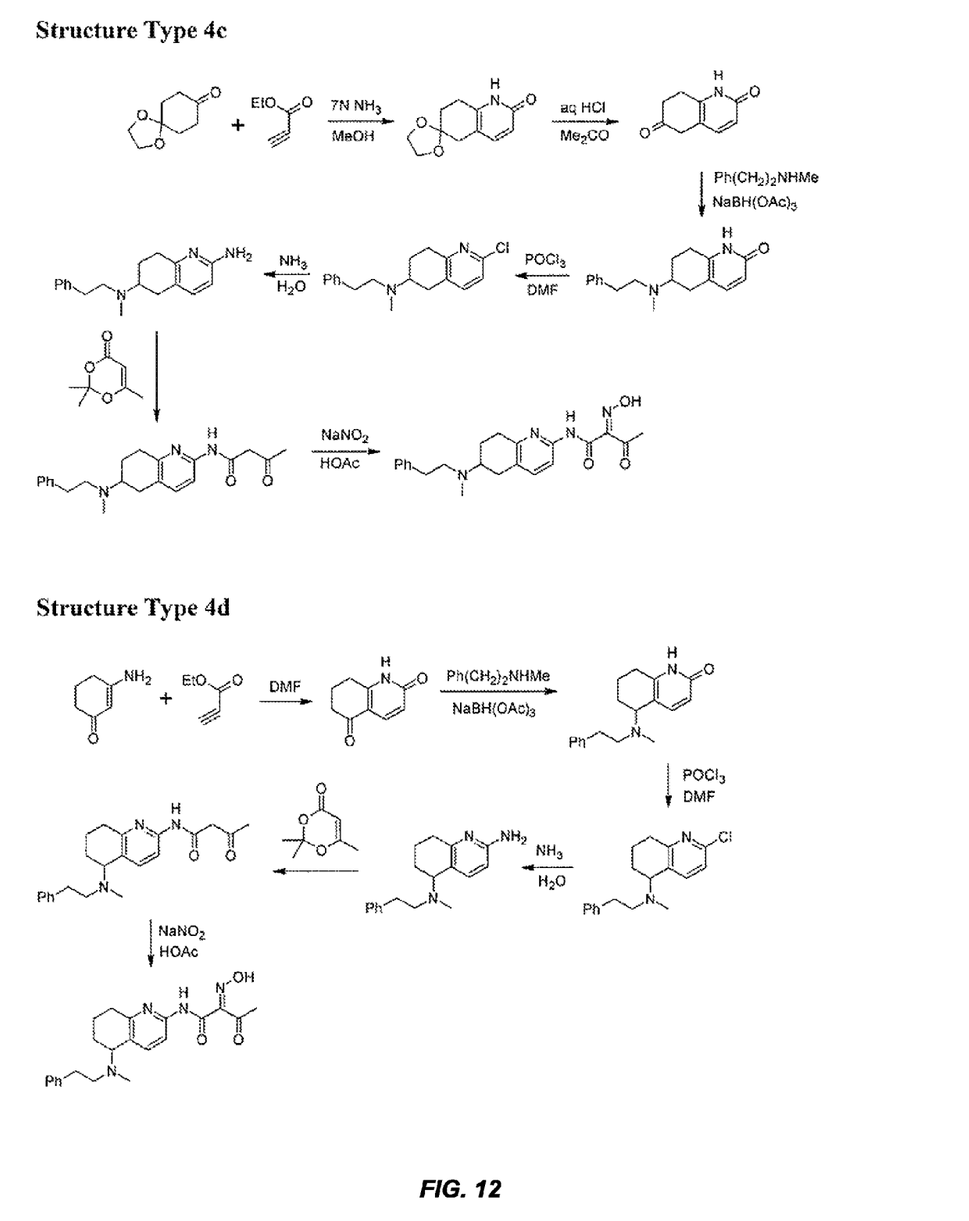
FIG. 12 illustrates the contemplated synthetic routes for Structure Type 4c and Structure Type 4d
Figure 13:
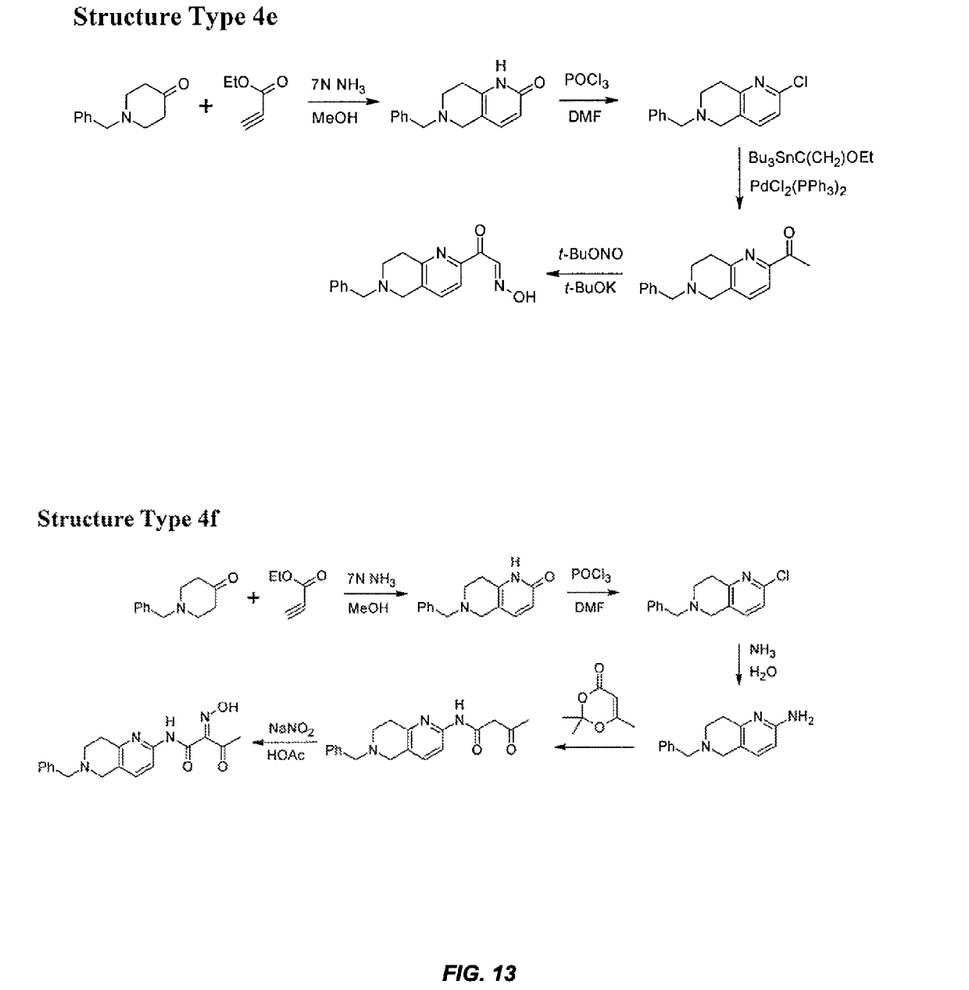
FIG. 13 illustrates the contemplated synthetic routes for Structure Type 4e and Structure Type 4f.

It may now be noted that a contemplated synthesis of the other reactivator type structures disclosed herein are shown in detail in FIGS. 5-13. Specifically, FIG. 5 illustrates the contemplated synthetic routes for Structure Type 1a and Structure Type 1b. FIG. 6 illustrates the contemplated synthetic routes for Structure Type 1c and Structure Type 1d. FIG. 7 illustrates the contemplated synthetic routes for Structure Type 2a and Structure Type 2b. FIG. 8 illustrates the contemplated synthetic routes for Structure Type 2c and Structure Type 2d. FIG. 9 illustrates the contemplated synthetic routes for Structure Type 3a and Structure Type 3b. FIG. 10 illustrates the contemplated synthetic routes for Structure Type 3c and Structure Type 3d. FIG. 11 illustrates the contemplated synthetic routes for Structure Type 4a and Structure Type 4b. FIG. 12 illustrates the contemplated synthetic routes for Structure Type 4c and Structure Type 4d. FIG. 13 illustrates the contemplated synthetic routes for Structure Type 4e and Structure Type 4f.

In vitro reactivation studies with (E)-2-(Hydroxyimino)-N-{6-[methyl(phenethyl)amino]-5,6,7,8-tetrahydroquinolin-3-yl}-3-oxobutanamide hydrochloride indicated a remarkably and unexpectedly high level of reactivation and a more rapid reactivation compared to other reactivators. In addition, the results support the finding that by positioning the oxime group adjacent a carbonyl of either a ketone or amide type functionality, which ketone or amide functionality is positioned adjacent a heteroaromatic or lactam type ring structure, enhanced reactivator characteristics are now observed. See again, FIGS. 1-3.

Moreover, once prepared, the reactivator compounds of FIGS. 1-3 may be readily incorporated into a pharmaceutically acceptable carrier. As noted, such compounds may then be administered in an antidotal amount to therapeutically treat exposure to an OP AChE inhibitor. A pharmaceutically acceptable carrier may therefore be understood herein as an aqueous formulation containing the above reactivators. Such formulations may therefore amount to aqueous solutions, suspensions and/or emulsions. Furthermore, it may be appreciated that an emulsion may be understood as an aqueous mixture containing the subject reactivator compounds in the presence of suitable hydrophobic/hydrophilic emulsifying agents and possibly other drugs.

In addition, the pharmaceutically acceptable aqueous carrier herein may include other diluents suitable for preparing oral pharmaceutical suspension. For example, an oral pharmaceutical suspension of the present invention may include, if necessary, pharmaceutically acceptable additives including auxiliary substances, stabilizing agents, suspending agents, surface tension modifiers, viscosity modifiers, colorants, preservatives, flavoring agents and other commonly used additives such as lactose, citric acid, tartaric acid, stearic acid, magnesium stearate, sucrose, and the like.

What is claimed is:

1. An acetylcholinesterase reactivator compound comprising the formula:

wherein $R_1$ is a ketone functionality (C(O)R) or hydrogen and R is a H or an alkyl group containing up to five carbon atoms;

$R_2$ is a hydrogen or an alkyl group containing up to five carbon atoms;

$R_3$ is a H;

Y is a carbon or nitrogen; and n has a value of 0-4.

2. A cholinesterase reactivator compound comprising the formula:

wherein $R_1$ is a ketone functionality (C(O)R) or hydrogen and R is a H or an alkyl group containing up to five carbon atoms;

$R_2$ and $R_4$ are hydrogen or an alkyl group containing up to five carbon atoms;

$R_3$ is a H;

Y is a carbon or nitrogen; and n has a value of 0-4.

3. The cholinesterase reactivator compound of claim 1, wherein $R_1$ is hydrogen.

4. The cholinesterase reactivator compound of claim 1, wherein $R_1$ is hydrogen and $R_2$ is —$CH_3$.

5. The cholinesterase reactivator compound of claim 1, wherein $R_1$ is hydrogen and $R_2$ is —$CH_3$.

6. The cholinesterase reactivator compound of claim 1, wherein $R_1$ is hydrogen, $R_2$ is —$CH_3$ and n is 1.

7. The cholinesterase reactivator compound of claim 1, wherein $R_1$ is hydrogen, $R_2$ is —$CH_3$, Y is —CH—, and n is 1.

8. The cholinesterase reactivator compound of claim 2, wherein $R_1$ is —(CO)$CH_3$.

9. The cholinesterase reactivator compound of claim 2, wherein $R_2$ is —$CH_3$ and $R_4$ is hydrogen.

10. The cholinesterase reactivator of claim 2, wherein $R_1$ is —(CO)$CH_3$, $R_2$ is —$CH_3$, and $R_4$ is hydrogen.

11. The cholinesterase reactivator compound of claim 2, wherein $R_1$ is —(CO)$CH_3$, $R_2$ is —$CH_3$, $R_4$ is hydrogen, and n is 1.

12. The cholinesterase reactivator compound of claim 2, wherein $R_1$ is —(CO)$CH_3$, $R_2$ is —$CH_3$, $R_4$ is hydrogen, Y is —CH—, and n is 1.

* * * * *